(12) United States Patent
Rynish

(10) Patent No.: US 6,277,105 B1
(45) Date of Patent: Aug. 21, 2001

(54) STRAIN RESISTANT STRIPS ARTICLE AND METHOD

(75) Inventor: Elizabeth M. Rynish, Fort Worth, TX (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/079,635

(22) Filed: May 15, 1998

(51) Int. Cl.[7] ....................................................... A61F 13/15
(52) U.S. Cl. ................................ 604/385.02; 604/385.03; 604/387; 604/389; 604/397; 604/401
(58) Field of Search ................................ 604/387, 385.2, 604/386, 389, 393, 397, 398, 401, 385.01, 385.03, 385.02, 385.04

(56) References Cited

U.S. PATENT DOCUMENTS

| | | |
|---|---|---|
| 3,044,467 | 7/1962 | Campau . |
| 3,315,677 | 4/1967 | Tyrrell, Jr. . |
| 3,397,697 | 8/1968 | Rickard . |
| 3,400,718 | 9/1968 | Saijo . |
| 4,753,645 | 6/1988 | Johnson . |
| 5,032,120 | * 7/1991 | Freeland et al. . |
| 5,037,418 | 8/1991 | Kons et al. . |
| 5,567,501 | 10/1996 | Srinivasan et al. . |
| 5,772,648 | * 6/1998 | Osborn, III et al. ............. 604/385.1 |

FOREIGN PATENT DOCUMENTS

| | | |
|---|---|---|
| 686219 | 2/1996 | (CH) . |
| 2260706 | 4/1993 | (GB) . |

* cited by examiner

Primary Examiner—Dennis Ruhl
(74) Attorney, Agent, or Firm—Thomas J. Connelly; Thomas M. Parker; Douglas G. Glantz

(57) ABSTRACT

A stain protection article and method are disclosed for providing protection against side leakage around a feminine care absorbent article. A pair of stain resistant strips have a stain protection sheet member aligned along a comfort cuff member shaped to accommodate the inside leg of a user. A garment-attachment adhesive on the stain resistant strips attaches to a crotch portion of an undergarment. The stain protection comfort cuff members are composed of an elastic barrier adhesive (EBA) material. The stain resistant strips article and method of the present invention further include providing a feminine care absorbent article completely separate from the pair of stain resistant strips and holding the feminine care absorbent article prior to use in a combination package formed from the first stain resistant strip and the second stain resistant strip. In one embodiment, the first stain resistant strip and the second stain resistant strip have arcuate shaped ends. In one aspect, the garment-attachment adhesive is positioned on a periphery of the pair of stain resistant strips.

3 Claims, 5 Drawing Sheets

STRAIN RESISTANT STRIPS ARTICLE AND METHOD

BACKGROUND OF THE INVENTION

1. Field of the Invention

This invention relates to a stain protection article and method for protecting a user's garments from body fluids including menstrual fluids and/or other body exudates. More specifically, this invention relates to a stain protection article and method for protecting a user's undergarment from side leakage of menstrual fluids around a feminine care absorbent pad.

2. Background of the Invention

Currently, wide varieties of products for the absorption of human body fluids are available in the form of feminine pads, sanitary napkins, panty shields, panty liners, and incontinence devices. Absorbent products for providing feminine care protection are designed to absorb body fluids, including menses, and come in different functional designs. Sanitary napkins and feminine care pads externally worn about the pudendal area are absorbent pads designed primarily for menstrual flow. Panty liners or panty shields are thin sanitary napkin products worn about the pudendal area for light menstrual flow. Absorbent products for providing incontinence protection are designed to absorb body fluids, including urine.

These absorbent products typically have an absorbent positioned between a liquid-permeable body side cover and a liquid-impermeable garment-facing baffle. These absorbent products include a top layer of the liquid-permeable body-side cover, a middle layer of the absorbent, and a bottom layer of the liquid-impermeable garment-facing baffle. A pressure sensitive adhesive typically is secured to the baffle. The pressure sensitive adhesive is used to attach the absorbent product to an inner crotch portion of a user's undergarment.

INTRODUCTION TO THE INVENTION

While feminine care absorbent products are commercially available and used widely today, a problem of leakage still persists. Menstrual fluids leak out around the sides of the feminine care absorbent products. Such side leakage stains a user's undergarments and outer garments.

Women today are drawn to use garments, including undergarments and outer garments, which are made from quality fabrics and construction. Staining by menstrual fluids generally ruins these garments made from quality fabrics having quality construction.

Accordingly, side leakage of menstrual fluids around the sides of a feminine care absorbent product is a serious concern of the feminine care absorbent product user.

Side flaps, tabs, wings, and other side constructions added onto the feminine care absorbent product have some success in absorbing the side leakage of menstrual fluids, but do not always absorb or contain all of the menstrual fluids, especially during periods of heavy flow. Side leakage, even with side flaps in place, sometimes is inevitable and almost always results in stains in a user's undergarments. However, even when the side flaps are effective in protecting the user's undergarments, an outer garment many times becomes stained.

Accordingly, there is a need for a stain protection article and method which provide protection against side leakage around the sides of a feminine care absorbent product. A stain protection article and method also are needed which prevent staining of undergarments and outer garments. A stain protection article and method also are needed which provide the user with a sense of comfort during use when full absorbency and full leakage protection are needed.

SUMMARY OF THE INVENTION

Briefly, the present invention provides a stain resistant strips article and method for protecting an undergarment from side leakage around a feminine care absorbent article, including a first stain resistant strip having a first strip stain protection sheet member and a first strip stain protection comfort cuff member aligned along the length of the first strip stain protection sheet member, wherein the first strip stain protection comfort cuff member is shaped to accommodate the inside leg of a user. A second stain resistant strip has a second strip stain protection sheet member and a second strip stain protection comfort cuff member aligned along the length of the second strip stain protection sheet member, wherein the second strip stain protection comfort cuff member is shaped to accommodate the inside leg of a user. A garment-attachment adhesive is provided for attaching the first strip stain protection sheet member and the second strip stain protection sheet member to a crotch portion of an undergarment. The first strip stain protection comfort cuff member and the strip stain protection comfort cuff member are composed of an elastic barrier adhesive (EBA) material.

The stain resistant strips article and method of the present invention further include providing a feminine care absorbent article completely separate from the first stain resistant strip and the second stain resistant strip and further include holding the feminine care absorbent article prior to use in a combination package formed from the first stain resistant strip and the second stain resistant strip.

In one aspect, the first stain resistant strip and the second stain resistant strip have arcuate shaped ends. In one aspect, the garment-attachment adhesive is positioned on a periphery of the first strip stain protection sheet member and on a periphery of the second strip stain protection sheet member for attaching to the crotch portion of an undergarment. In one embodiment, the first stain resistant strip and the second stain resistant strip have arcuate shaped ends.

A general object of the present invention is to provide a stain protection article and method which prevent staining of a user's undergarment.

Another general object of the present invention is to provide a stain protection article and method which prevent staining of outer garments.

It is an object of the present invention to provide a stain protection article and method which protect against side leakage around the sides of a feminine care absorbent product.

It is an object of the present invention to provide a stain protection article in a combination package with a feminine care absorbent product.

It is an object of the present invention to provide a stain protection article in a combination package with a feminine care absorbent product having packaging manufacturing cost advantages.

It is an object of the present invention to provide a stain protection article in a combination package with a feminine care absorbent product having cost of material packaging advantages.

A further object of the present invention is to provide a stain protection article in a combination package with a feminine care absorbent product which uses less packaging material.

It is an object of the present invention to provide an accurate and convenient placement and a secure positioning of the stain protection article of the present invention.

A more specific object of this invention is to provide a stain protection article and method which provide the user with a sense of comfort during use when full absorbency and full leakage protection are needed.

These and other objects and advantages of the present invention will become more apparent to those skilled in the art in view of the following detailed description and the accompanying drawings.

DETAILED DESCRIPTION OF THE PREFERRED EMBODIMENTS

Figure 1:
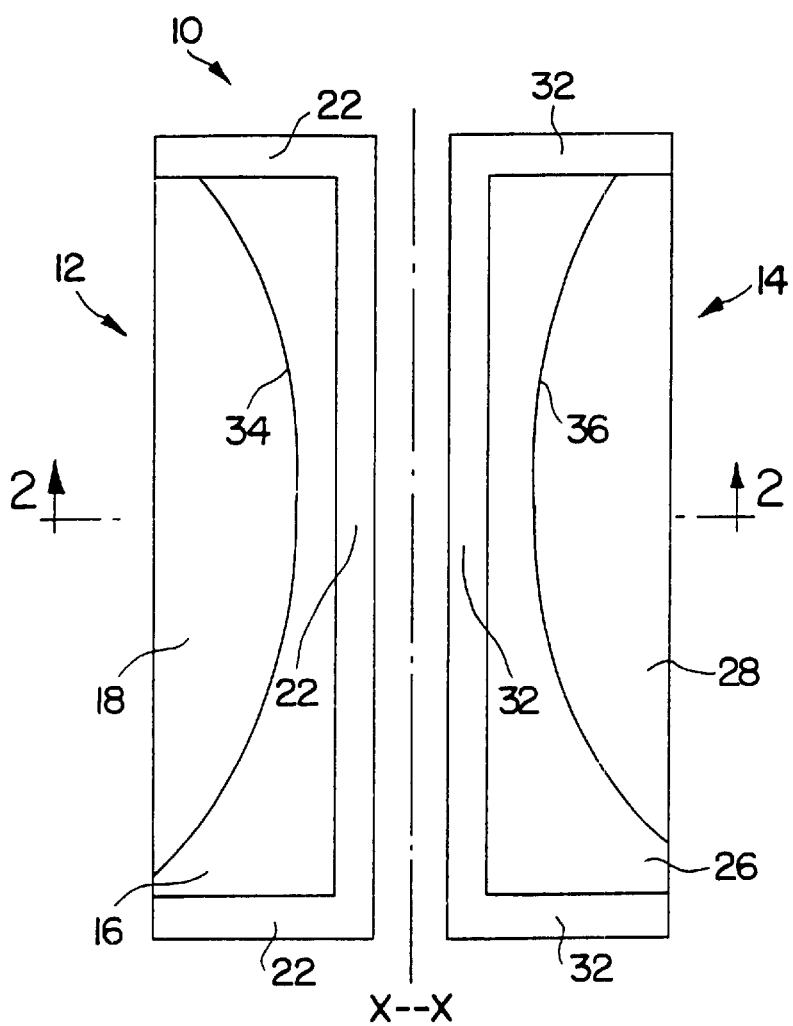
FIG. 1 is a top plan view of a stain protection article of the present invention.
Figure 2:
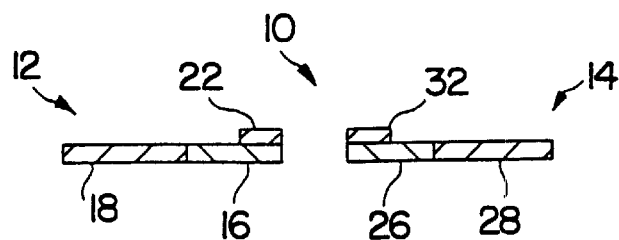
FIG. 2 is a cross sectional view, taken along line 2—2 of FIG. 1, of a stain protection article of the present invention.

Referring now to FIGS. 1 and 2, a stain resistant strips article 10 is shown as having a pair of stain resistant strips 12 and 14 for use in connection with attachment to an undergarment of the wearer. A left stain resistant strip 12 as viewed in FIG. 1 has a stain protection sheet member 16 and a stain protection comfort cuff member 18. The stain protection sheet member 16 is positioned adjacent the stain protection comfort cuff member 18 and is aligned with the stain protection comfort cuff member 18 along the longitudinal axis X—X. The stain protection sheet member 16 is attached to the stain protection comfort cuff member 18 by ultrasonic bonding, thermal bonding, and/adhesive bonding. In a preferred embodiment, The stain protection sheet member 16 is attached to the stain protection comfort cuff member 18 by adhesive applied under pressure and thermally cured.

An adhesive strip 22 is provided around a perimeter of the stain protection sheet member 16 along the three sides of the stain protection sheet member 16 which are not aligned with the stain protection comfort cuff member 18.

A right stain resistant strip 14 as viewed in FIG. 1 has a stain protection sheet member 26 and a stain protection comfort cuff member 28. The stain protection sheet member 26 is positioned adjacent the stain protection comfort cuff member 28 and is aligned with the stain protection comfort cuff member 28 along the longitudinal axis X—X. An adhesive strip 32 is provided around a perimeter of the stain protection sheet member 26 along the three sides of the stain protection sheet member 26 which are not aligned with the stain protection comfort cuff member 28.

The stain protection comfort cuff members 18 and 28 have an inside length 34 and 36, respectively, in a shape configured to accommodate the arcuate shape of the inside of a user's leg.

The stain resistant strips 12 and 14 of the present invention are attached to an outer edge of the undergarment by the adhesive strips 22 and 32 which stick to the cloth fabric or other material of the undergarment.

The stain resistant strips article 10 provides protection against stains to make underwear for women more durable and last longer. Women's underwear currently available today is not stain resistant. When menstruating, a women uses a feminine care absorbent pad, but still it is normal to have menses overflow onto undergarments and onto clothes. Overflow also occurs during every day deposits. The stain resistant strips article of the present invention provides women with security from menstrual overflow, protecting the undergarment and clothes from staining leading to material deterioration.

It is an important aspect that the stain resistant strips article of the present invention is provided by an article separate from the feminine care absorbent article, i.e., provided by a stain protection article completely separated and entirely physically discrete from the feminine care absorbent article. I have found that when using feminine care absorbent articles available commercially today, a consumer sometimes experiences side leakage around the feminine care absorbent article and such side leakage almost always causes staining of her undergarments or clothes. There are several reasons for the fact that, no matter what, side leakage and staining is experienced. These reasons are based on three components which can not be controlled by the supplier of the feminine care absorbent articles available commercially today. These three components are (1) temperature, (2) body size, and (3) the feminine care absorbent article attachment surface.

The supplier of the feminine care absorbent articles available commercially today can not control the temperature at which the feminine care absorbent articles are used. When the temperature varies, the feminine care absorbent articles available commercially today do not function in such a way so as to be fail safe because additional heat stresses the pad and causes it to deform.

The supplier of the feminine care absorbent articles available commercially today can not control the body size of the user. When the body size varies, the feminine care absorbent articles available commercially today do not function in such a way so as to be fail safe because variable thigh sizes and variable crotch lengths and widths cause the absorbent article to fit differently on each person.

The supplier of the feminine care absorbent articles available commercially today can not control the surface on which the user attaches the feminine care absorbent article. When the surface of attachment varies, the feminine care absorbent articles available commercially today do not function in such a way so as to be fail safe because the nature of the different fabrics causes varying pad attachment stability. For example, a quality spandex as a surface of attachment performs differently from an inexpensive nylon as a surface of attachment, which performs differently from cotton as a surface of attachment. The supplier of the feminine care absorbent article has no control over the material used as the surface of attachment. The pressure sensitive adhesive of the feminine care absorbent article works on cotton fabric in a manner different from polyester.

When the feminine care absorbent articles available commercially today are applied to the undergarment, many times the undergarment becomes clumped up, e.g., in a roller coaster pattern, and the undergarment is not fully protected from staining.

For these reasons, the feminine care absorbent articles available commercially today never fully and completely fit. Accordingly, an important aspect of the stain resistant strips article and method of the present invention is found in providing a stain resistant strips article separate from the feminine care absorbent article.

Left strip 12 and right strip 14 as viewed in FIG. 1 are depicted as having an overall rectangular shape, but strips 12 and 14 can take the form of other shapes, e.g., such as by way of example, an oval, a flat oval, or a rectangle having arcuate ends, so long as the strips are attached to the undergarment with enough surface area to provide a secure attachment and the comfort cuff provides enough surface area for containing the menstrual fluids.

The stain protection sheet members 16 and 26 are composed of a sheet of liquid-impermeable material or of a material that can absorb the overflow together with a liquid-impermeable undersheet, e.g., by way of example, a light and thin conform or cellulose material. The stain protection comfort cuff members 18 and 28 are composed of a stretchable material which grips gently the leg of a user, e.g., by way of example, in a manner such as provided by elastic barrier adhesive (EBA) material. The adhesive strips 22 and 32 are composed of a strip of pressure sensitive adhesive material.

It has been found that stain protection comfort cuff members 18 and 28 preferably are composed of a stretchable material which has not been stretched. When the stretchable material becomes stretched before being placed into use, the comfort cuff does not work properly in the stain resistant article and method of the present invention, but rather pulls the undergarment fabric into an undesirably rippled condition.

The elastic barrier adhesive (EBA) material as used in the comfort cuff members 18 and 28 of the stain resistant strips article of the present invention preferably is formed from one layer of spunbond, a middle layer of stretchable melt blown film, and another layer of spunbond. It has been found that the stain resistant strips article and method of the present invention providing a stain resistant comfort cuffs member composed of elastic barrier adhesive (EBA) material works well to prevent staining and is significantly more comfortable and non-chafing to the user than other materials, such as elastic alone or elastic placed between two layers of non-woven material.

Figure 3:
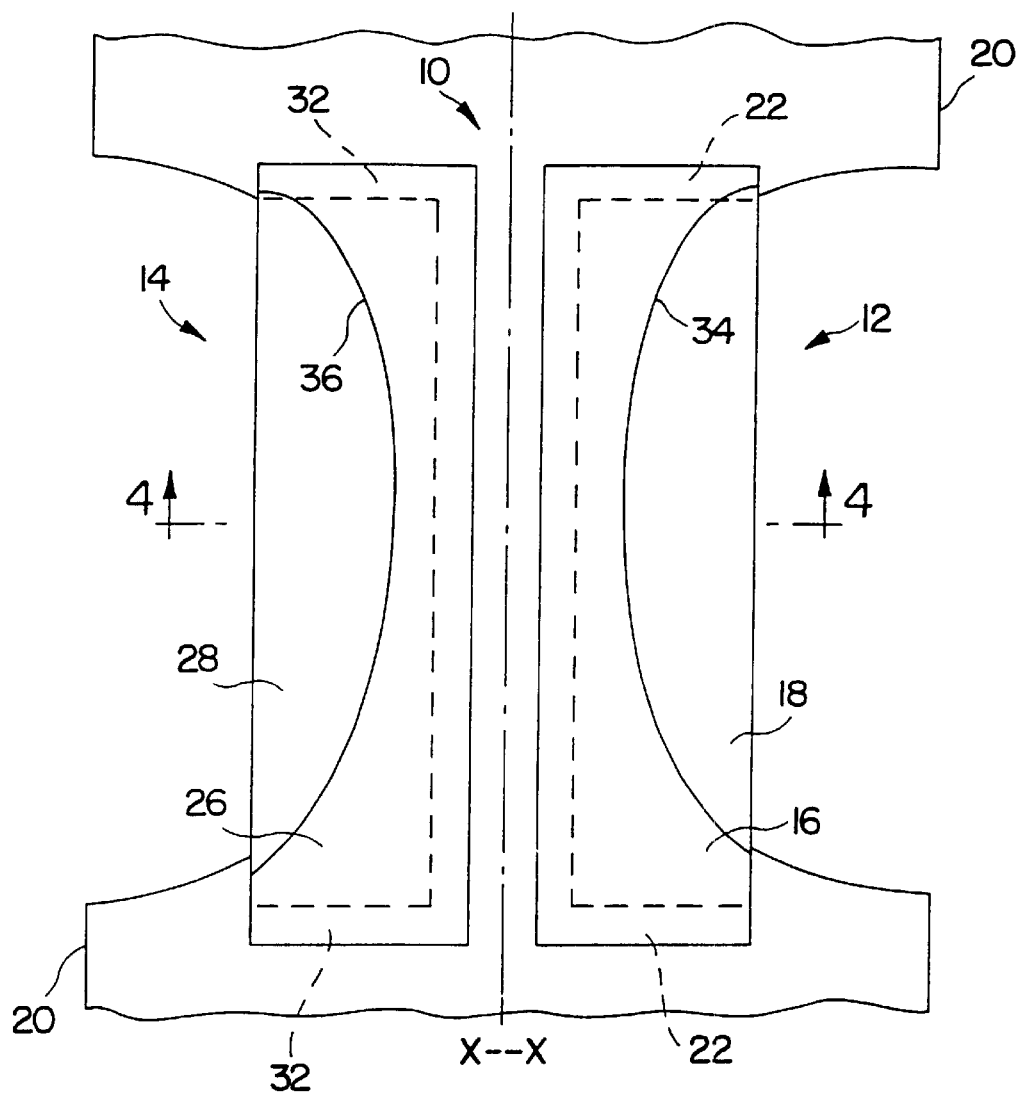
FIG. 3 is a top plan view of a stain protection article of the present invention attached to the crotch portion of a user's undergarment.
Figure 4:
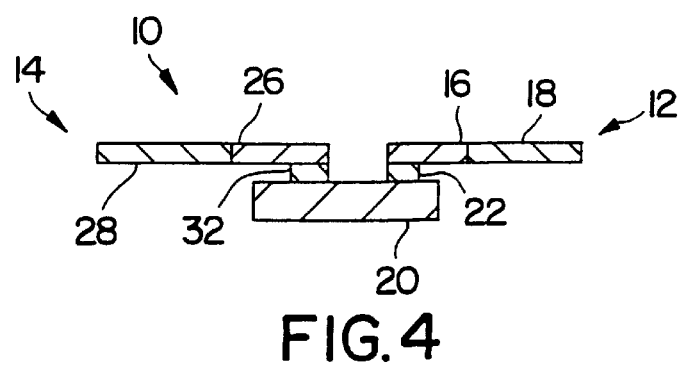
FIG. 4 is a cross sectional view, taken along line 4—4 of FIG. 3, of a stain protection article of the present invention attached to the crotch portion of a user's undergarment.

Referring now to FIGS. 3 and 4, a stain resistant strips article 10 is shown as having a pair of stain resistant strips 12 and 14 for use in connection with attachment to an undergarment 20 of the wearer. A right stain resistant strip 12 as viewed in FIG. 3 has a stain protection sheet member 16 and a stain protection comfort cuff member 18. Because the stain resistant strips article 10 is shown applied to the undergarment 20 in FIG. 3, the side designations 12 and 14 referenced in FIG. 1 are reversed for FIG. 3. The stain protection sheet member 16 is positioned adjacent the stain protection comfort cuff member 18 and is aligned with the stain protection comfort cuff member 18 along the longitudinal axis X—X. An adhesive strip 22 is provided around a perimeter of the stain protection sheet member 16 along the three sides of the stain protection sheet member 16 which are not aligned with the stain protection comfort cuff member 18. A left stain resistant strip 14 as viewed in FIG. 3 has a stain protection sheet member 26 and a stain protection comfort cuff member 28. The stain protection sheet member 26 is positioned adjacent the stain protection comfort cuff member 28 and is aligned with the stain protection comfort cuff member 28 along the longitudinal axis X—X. An adhesive strip 32 is provided around a perimeter of the stain protection sheet member 26 along the three sides of the stain protection sheet member 26 which are not aligned with the stain protection comfort cuff member 28.

The stain protection comfort cuff members 18 and 28 have an inside length 34 and 36, respectively, in a shape configured to accommodate an arcuate shape of an inside of a user's leg.

The stain resistant strips 12 and 14 of the present invention are attached to a top surface of the undergarment 20 by the adhesive strips 22 and 32, respectively, which stick to the cloth fabric or other material of the undergarment 20.

Figure 5:
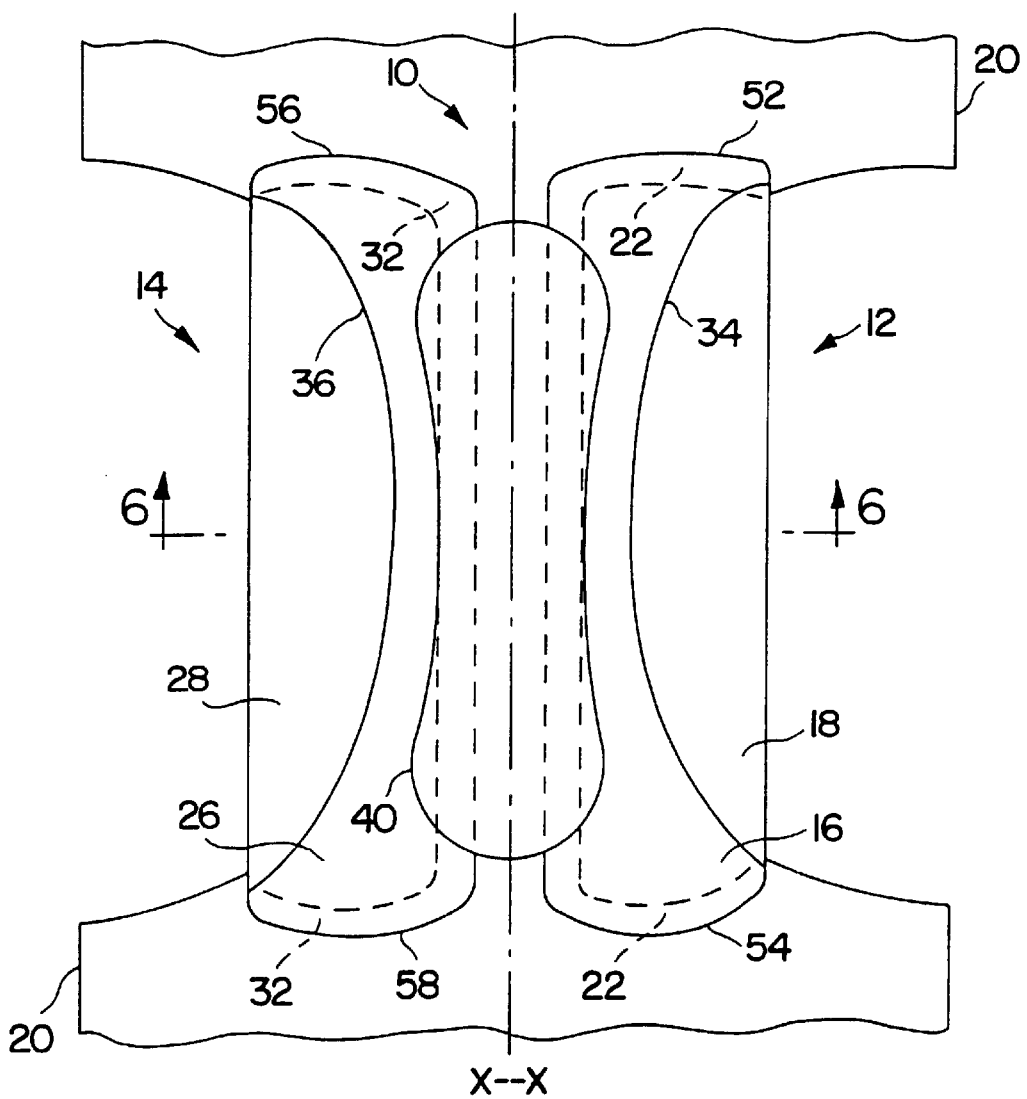
FIG. 5 is a top plan view of a stain protection article of the present invention and a feminine care absorbent article attached to the crotch portion of a user's undergarment.
Figure 6:
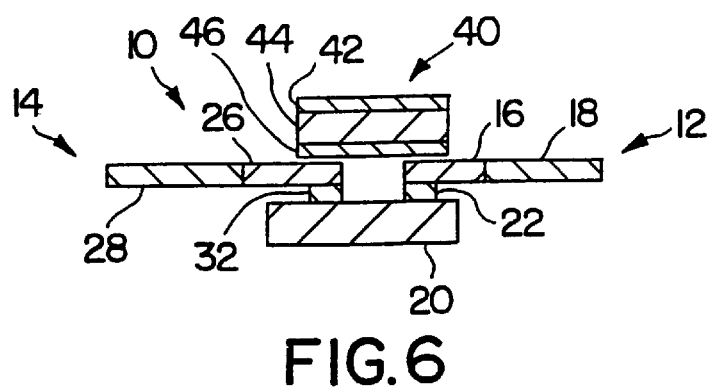
FIG. 6 is a cross sectional view, taken along line 6—6 of FIG. 5, of a stain protection article of the present invention and a feminine care absorbent article attached to the crotch portion of a user's undergarment.

Referring now to FIGS. 5 and 6, a stain resistant strips article 10 is depicted in connection with a feminine care absorbent article 40, e.g., such as a feminine care sanitary napkin. The stain resistant strips article and method of the present invention also have application to other absorbent article embodiments, such as a feminine care panty liner or a panty shield, an incontinent garment, a urinary shield, or an underarm pad. For purposes of illustration, the absorbent article 40 will be described as a feminine care absorbent article.

The stain resistant strips article 10 is shown as having a pair of stain resistant strips 12 and 14 for use in connection with attachment to an undergarment 20 of the wearer. A right stain resistant strip 12 as viewed in FIG. 5 has ends 52 and 54 shaped in an arcuate configuration. A left stain resistant strip 14 has ends 56 and 58 shaped in an arcuate configuration.

The absorbent article 40 is depicted in position on top of stain resistant strips article 10. Pressure sensitive adhesive is placed in the center of the underside of the absorbent article 40 to hold absorbent article 40 in position on top of the satin resistant strips article 10 of the present invention.

The absorbent article 40 includes a liquid-permeable cover 42, an absorbent 44, and a liquid-impermeable baffle 46. The absorbent 44 is positioned between the liquid-permeable cover 42 and the liquid-impermeable baffle 46. The absorbent article 40 is constructed to form layers of the liquid-permeable cover 42, the absorbent 44, and the liquid-impermeable baffle 46, vertially arranged.

The liquid-permeable cover 42 is made of a material designed to serve functionally as the material which will come into contact with a wearer's body. The liquid-permeable cover 42 is made from a woven or non-woven, natural or synthetic material which is readily penetrated by body fluids. Thermoplastic polymer films made from fibers or filaments of polyethylene or polypropylene are preferred.

Cover 42 has apertures (not shown) formed in the cover 42 to increase the rate at which the body fluids penetrate through the cover 42 into the absorbent 44.

The absorbent 44 is hydrophilic and is made of cellulose fibers, wood pulp, regenerated cellulose, cotton fibers, or a blend of pulp and other fibers. The absorbent 44 usually is resilient for enabling the absorbent article 40 to bend easily without excessive distortion. Hydro colloidal material, commonly referred to as super absorbents, can be added to the hydrophilic material to increase the absorption capacity of the absorbent article 40.

The absorbent article 40 provides service as a sanitary napkin, a panty liner, or a panty shield pad, and comes into attachment with the stain resistant strips article 10. The liquid-impermeable baffle 46 of the absorbent article 40 faces an inner surface, i.e., body-facing surface, of the stain resistant strips article 10.

The first strip stain protection sheet member 18, the second strip stain protection sheet member 28, and the baffle 46 can be made from a polymeric film such as polyethylene, polypropylene, or cellophane, or can be made from a bi-component film. A preferred material is ethyl-vinyl-acetate/polyethylene co-extruded film. In one aspect, the first strip stain protection sheet member 18, the second strip stain protection sheet member 28, and the baffle 46 can be constructed from a liquid-permeable material that has been treated or coated to become liquid-impervious.

The cover 42 and the baffle 46 can be attached or joined together, such as by a peripheral seal, to enclose the absorbent 44. The cover 42 can be wrapped entirely about the absorbent 44, and then the baffle 46 can be attached to the lower surface of the cover 42 by end seals.

The absorbent article 40 usually has an overall length of between about 6 to 12 inches (15 to 30 cm) and a width of between about 2 to 3.5 inches (5 to 9 cm), sometimes about 1.5 to 3.5 inches (4 to 9 cm). The thickness of absorbent article 40 can vary form about 2 mm to about one inch (2.5 cm).

The stain resistant strips article 10 used in combination with the absorbent article 40 usually has an overall length of between about 4 to 15 inches (10 to 38 cm) and a width of between about 1.5 to 4 inches (3.5 to 10 cm), sometimes about 4 to 10 inches (10 to 25 cm). The thickness of stain resistant strips article 10 can vary form about 1 mm to about 0.5 inch (1.5 cm).

Figure 7:
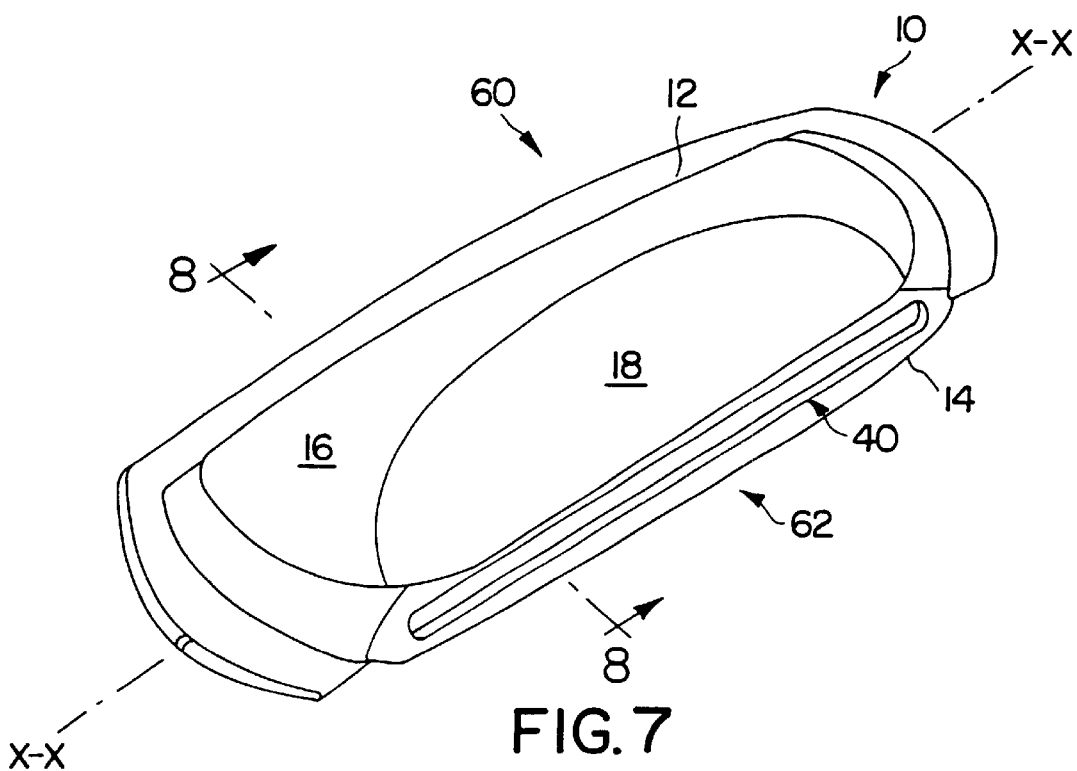
FIG. 7 is a perspective view of a stain protection article of the present invention and a feminine care absorbent article in a combination package of the present invention.
Figure 8:
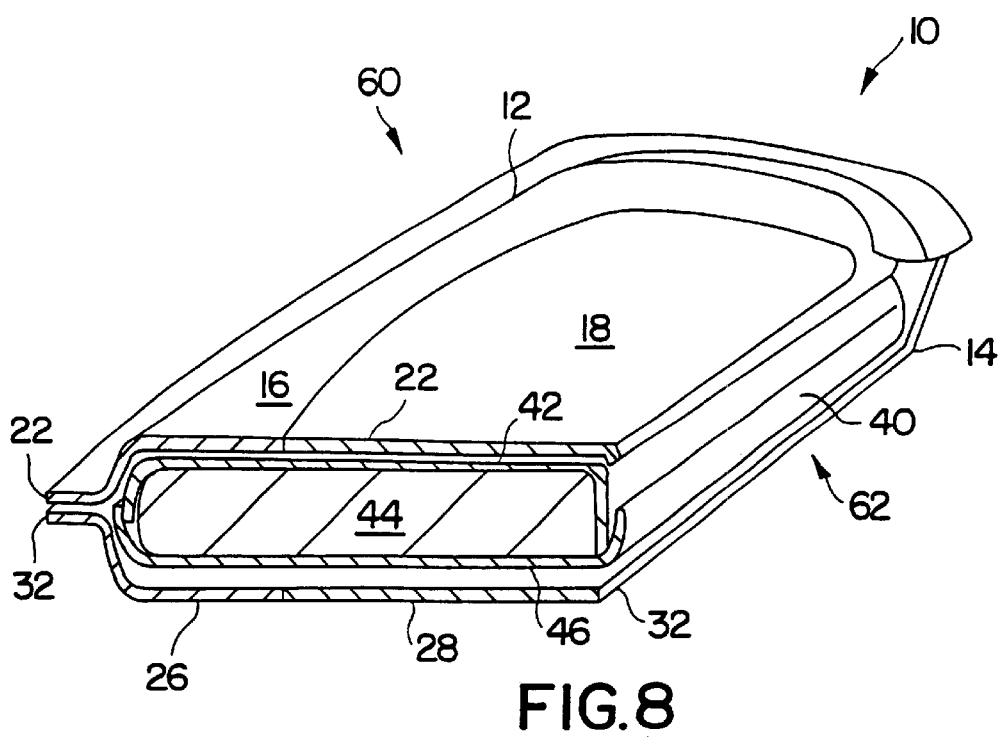
FIG. 8 is a cross sectional view, taken along line 8—8 of FIG. 7, of a stain protection article and feminine care absorbent article combination package of the present invention.

Referring now to FIGS. 7 and 8, a stain resistant strips article 10 is depicted with a feminine care absorbent article 40, e.g., such as a feminine care sanitary napkin, in a combination package 60.

Combination package 60 has a pocket 62 formed by matching up sides 12 and 14 of stain resistant strips article 10. Absorbent article 40 is nested into pocket 62.

Figure 9:
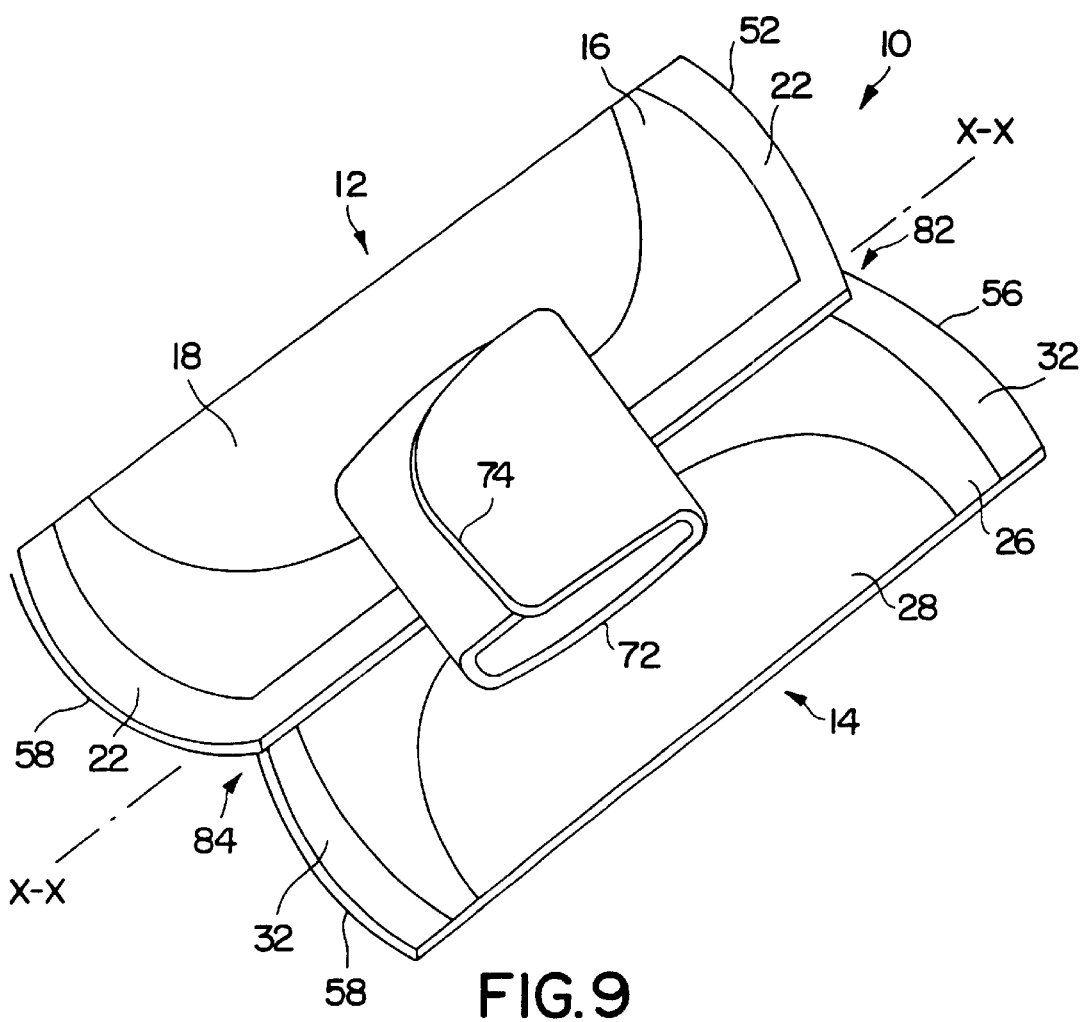
FIG. 9 is a perspective view of a stain protection article of the present invention and a tri-folded feminine care absorbent article in a combination package of the present invention.
Figure 10:
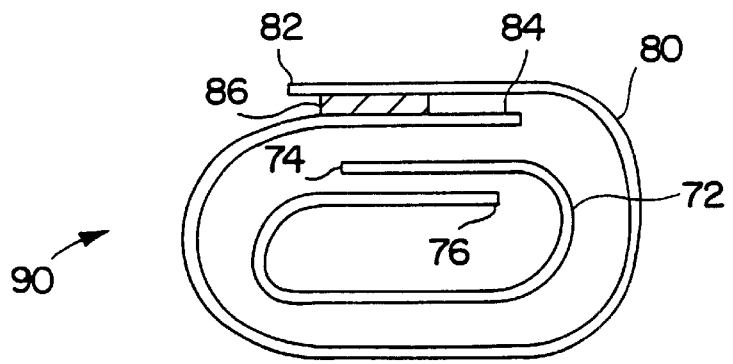
FIG. 10 is a side elevation view of a tri-folded stain protection article of the present invention and a tri-folded feminine care absorbent article in a combination package of the present invention.

Referring now to FIGS. 9 and 10, a stain resistant strips article 10 is tri-folded to form a stain resistant strips article 80 shown depicted with a tri-folded feminine care absorbent article 72, e.g., such as a tri-folded feminine care sanitary napkin, in a combination package 90.

Left side stain resistant strip 14, as shown in FIG. 9, is overlapped onto right side stain resistant strip 12. The tri-folded absorbent article 72 has a first folded end 74 and a second folded end 76. The absorbent article 72 is tri-folded, i.e., folded twice to form three folded members forming a folded absorbent article measuring about three inches by three inches (8 cm by 8 cm).

The tri-folded absorbent article 72 is positioned in the middle of the stain resistant strips article 10, as shown in FIG. 9, having overlapped strips 12 and 14. The overlapped stain resistant strips article 10 has one end 82 and an opposite end 84. The tri-folded absorbent article 72 is positioned between the one end 82 and the opposite end 84 of the overlapped stain resistant strips article 10.

The stain resistant strips article 10 then is tri-folded, i.e., folded twice to form three folded members forming a folded absorbent article. The tri-folded stain resistant strips article 80 has one end 82 and an opposite end 84. The tri-folded stain resistant strips article 80 has an adhesive 86 applied to the one end 82 to hold it in place in a tri-folded condition over the opposite end 84. The adhesive has a light tack so that the stain resistant strips can be unfolded and used to protect a user's undergarments in the manner of the method of the present invention. In one embodiment, the pressure sensitive adhesive 22 and/or the pressure sensitive adhesive 32 can serve the function of adhesive 86 to hold the stain resistant strips article 80 temporarily in a tri-folded condition, and then in that embodiment, adhesive 86 is replaced by the pressure sensitive adhesive 22 and/or 32 of the stain resistant strips article 80.

In FIG. 10, a tri-folded stain protection article 80 is shown tri-folded around tri-folded feminine care absorbent article 72. Accordingly, a combination package 90 of the present invention is shown having a tri-folded stain protection article 72 and a tri-folded feminine care absorbent article 80. The tri-folded absorbent article 72 is nested into the center of the tri-folded stain resistant strips article 80, as shown in FIG. 10.

The absorbent article 40 and 72 as used in the combination package 60 and 90 of the present invention can be formed in the shape of a race track or oval or the like. The absorbent article 40 and 72 can have other shapes, e.g., such as rectangular shapes other than oval or race track shape, provided that the shapes are designed to cover the pudendal region of a woman. The absorbent article 40 can be viewed as having a central longitudinal axis X—X. Most absorbent pad articles, such as sanitary napkins and panty liners or shields, are layered in sheets which are longer than they are wide. In addition to the liquid-permeable cover 42, the absorbent 44, and the baffle 46, other layers also can be utilized, such as a transfer layer, a layer of anhydrous deodorant material, a layer containing super-absorbent materials, and additional absorbent layers.

The various layers can be vertically stacked, assembled, laminated, and/or bonded together to form the sheet or web of material from which the articles are later cut or stamped out, prior to attachment of the liquid-impermeable baffle of the present invention. The various layers can be bonded together by using heat, pressure, heat and pressure, adhesive, hot melt glue, stitching with thread, ultrasonic bonding, mechanical bonding, thermal bonding, chemical bonding, or a combination of these and/or other means known to those skilled in the art.

The first strip stain protection sheet member 18, the second strip stain protection sheet member 28, and the liquid-impermeable baffle 46 can be designed to permit the passage of air or vapor out of the absorbent articles while blocking the passage of body fluid. The first strip stain protection sheet member 18, the second strip stain protection sheet member 28, and the liquid-impermeable baffle 46 can be made from any material having these properties. The first strip stain protection sheet member 18, the second strip stain protection sheet member 28, and the liquid-impermeable baffle 46 also can be constructed from a material that will block the passage of vapor as well as fluids, if desired. A good material from which the first strip stain protection sheet member 18, the second strip stain protection sheet member 28, and the liquid-impermeable baffle 46 can be constructed is a micro-embossed, polymeric film, such as polyethylene or polypropylene. Bi-component films also can be used. A preferred material is polyethylene film. Most preferably, the polyethylene film will have a thickness in the range of from about 0.5 mil to about 2.0 mil.

Construction adhesive can be used in the articles of the present invention to attach and bond the various layers together. For example, referring to FIG. 6, a construction adhesive can be used to bond the liquid-impermeable baffle 46 to the absorbent 44 or to bond the absorbent 44 to the liquid-permeable cover 42. The presence of such a construction adhesive and the amount used will depend upon manufacturing specifications. Useful construction adhesives are commercially sold by National Starch and Chemical Company, having an office located at 10 Finderne Ave., Bridgewater, N.J. 08807.

The liquid-permeable cover 42 is designed to contact the body of the wearer and can be constructed of a woven or non-woven material which is easily penetrated by body fluid. The liquid-permeable cover 42 also can be formed from either natural or synthetic fibers. Suitable materials include bonded carded webs of polyester, polypropylene, polyethylene, nylon, or other heat-bondable fibers. Other polyolefins, such as copolymers of polypropylene and polyethylene, linear low-density polyethylene, finely-perforated film webs and net materials, also work well. A preferred material is a composite of an apertured thermoplastic film positioned above a non-woven fabric material. Such a composite material can be formed by extrusion of a polymer onto a web of spunbond material to form an integral sheet. One example of this material is an apertured, thermoplastic polyethylene film bonded to a spunbond material. Spunbond material is a non-woven material which is manufactured and commercially sold by Kimberly-Clark Corporation having an office located at 401 N. Lake Street, Neenah, Wis. 54956. The apertured film/non-woven laminate exhibits a smooth appearance and is soft to the touch. This material is soft and does not irritate the wearer's skin and yet has a cushioned feel because of its bulk. Another material useful as the liquid-permeable cover 42 is a spunbond web of polypropylene. This spunbond web can contain from between about 1 percent to about 6 percent of a whitening agent, such as titanium dioxide ($TiO_2$) or calcium carbonate ($CaCO_3$) to give it a clean, white appearance. A uniform thickness of spunbond is desirable because it will have sufficient strength, after being perforated, to resist being torn or pulled apart during use. The most preferred polypropylene webs have a basis weight of between about 18 grams per square meter ($g/m^2$) to about 40 $g/m^2$. An optimum weight is between about 30 $g/m^2$ to about 40 $g/m^2$.

The absorbent layer 44 can be present as a single layer or as two or more distinct layers. The absorbent layer 44 can be formed from various natural or synthetic fibers such as wood pulp fibers, virgin cellulose fibers, regenerated cellulose fibers, cotton fibers, peat moss, or a blend of pulp and other fibers. The absorbent layer 44 also could be formed from a fine pore fabric such as wet-laid, air-dried tissue or from an uncreped through air-dried (UCTAD) tissue having a basis weight of from about 30 $g/m^2$ to about 120 $g/m^2$. The UCTAD tissue can be prepared by a process disclosed in U.S. Pat. No. 5,048,589 issued to Crook et al. on Sep. 17, 1991. The UCTAD tissue is disclosed in U.S. Pat. No. 5,399,412 issued to Sudall et al. on Mar. 21, 1995. Each of these patents is incorporated by reference and made a part hereof. The absorbent layer 44 also may be comprised of other well-known materials such as cellulose fibers, rayon fibers, cellulose sponge, hydrophilic synthetic sponge, for example polyurethane, and the like.

The absorbent article 40 also includes one or more elongated strips or areas of an attachment adhesive secured to the bottom surface of the liquid-permeable baffle 46. The attachment adhesive functions to attach the absorbent article 40 to the inner crotch portion of the undergarment 20 and to overlap a portion of the stain resistant article 10. The attachment adhesive can cover a portion of the bottom surface of the liquid-impermeable baffle 46.

The attachment adhesive 22 and 32 of the stain resistant article 10 and of the feminine care absorbent article 40 can consist of a swirl pattern of adhesive or be one or more strips of adhesive or various other patterns. The attachment adhesive also can consist of a plurality of adhesive dots which are randomly or uniformly arranged on the exterior surface of the first strip stain protection sheet member 18, the second strip stain protection sheet member 28, and the baffle 46. The attachment adhesive can be aligned in a single wide strip, or alternatively, the attachment adhesive can be present as two or more spaced apart longitudinal strips. The attachment adhesive is of such a nature that it will allow the user to remove the stain resistant article 10 and of the feminine care absorbent article 40 and reposition it on her undergarment if needed. A hot melt adhesive which works well as the garment attachment adhesive 22 and 32 of the stain resistant article 10 and for the attachment adhesive of the feminine care absorbent article 40 is commercially sold by National Starch and Chemical Company having an office located at 10 Finderne Avenue, Bridgewater, N.J. 08807.

In order to protect the garment attachment adhesive from contamination or drying prior to use, the adhesive can be protected by a releasable peel strip. The release strip can be a white Kraft paper which is coated on one side so that it can be released from the adhesive. The coating can be a silicone coating, such as a silicone polymer commercially available from Akrosil having an office located at 206 Garfield Avenue, Menasha, Wis. 54952. The release strips can be removed by the user prior to attachment of the stain protection article 10 or the absorbent article 40 to the inner crotch portion of her undergarment 20.

The stain protection method of the present invention includes providing a first stain resistant strip having a first strip stain protection sheet member and having a first strip stain protection comfort cuff member aligned along the length of the first strip stain protection sheet member, wherein the first strip stain protection comfort cuff member is shaped to accommodate the inside leg of a user; providing a second stain resistant strip having a second strip stain protection sheet member and having a second strip stain protection comfort cuff member aligned along the length of the second strip stain protection sheet member, wherein the second strip stain protection comfort cuff member is shaped to accommodate the inside leg of a user positioning a liquid-impermeable baffle on a bottom side of the absorbent; and providing a garment-attachment adhesive on the first strip stain protection sheet member and the second strip stain protection sheet member for attaching to a side surface of a crotch portion of an undergarment.

The method of protecting a user's undergarment further includes providing a first strip stain protection comfort cuff member and a second strip stain protection comfort cuff member composed of an elastic barrier adhesive (EBA) material.

The novel method of the present invention includes providing a feminine care absorbent article completely separate from the first stain resistant strip and the second stain resistant strip.

The novel method of the present invention further includes packaging the first stain resistant strip, the second stain resistant strip, and the feminine care absorbent article in a combination package formed from the first stain resistant strip and the second stain resistant strip.

Now, a stain protection article and method have been developed which provide a user with protection against side leakage around a feminine care absorbent article, which prevent staining of undergarments and outer garments, and which provide a combination package with lower packaging manufacturing costs and lower packaging material production costs. The stain protection article and method provide the user with a sense of comfort during use together with full absorbency and full leakage protection.

While the invention has been described in conjunction with several embodiments, it is to be understood that many alternatives, modifications, and variations will be apparent to those skilled in the art in light of the foregoing description. Accordingly, this invention is intended to embrace all such alternatives, modifications, and variations which fall within the spirit and scope of the appended claims.

What is claimed is:

1. A stain protection article, comprising:

(a) a first stain resistant strip having a first strip stain protection sheet member and having a first strip stain protection comfort cuff member aligned along the length of said first strip stain protection sheet member, wherein said first strip stain protection comfort cuff member is shaped to accommodate the inside leg of a user;

(b) a second stain resistant strip having a second strip stain protection sheet member and having a second strip stain protection comfort cuff member aligned along the length of said second strip stain protection sheet member, wherein said second strip stain protection comfort cuff member is shaped to accommodate the inside leg of a user;

(c) a garment-attachment adhesive on said first strip stain protection sheet member and said second strip stain protection sheet member for attaching to a crotch portion of an undergarment;

(d) a feminine care absorbent article separate from said first stain resistant strip and said second stain resistant strip;

(e) a combination package for holding said feminine care absorbent article prior to use, wherein said combination package is formed from said first stain resistant strip and said second stain resistant strip; and (f) wherein said first stain resistant strip and said second stain resistant strip have arcuate shaped ends and further are composed of a bi-component web material of ethyl-vinyl-acetate/polyethylene co-extruded film.

2. The stain protection article of claim 1, wherein said garment-attachment adhesive is positioned on a periphery of said first strip stain protection sheet member and on a periphery of said second strip stain protection sheet member for attaching to said crotch portion of an undergarment.

3. The stain protection article of claim 2, wherein said first stain protection sheet member is attached to said stain protection comfort cuff member by adhesive applied under pressure and thermally cured.

* * * * *